United States Patent [19]

Albright et al.

[11] Patent Number: 4,493,323

[45] Date of Patent: Jan. 15, 1985

[54] SUTURING DEVICE AND METHOD FOR USING SAME

[75] Inventors: John P. Albright; Robert K. Martin; John A. Dyson, all of Iowa City, Iowa

[73] Assignee: University of Iowa Research Foundation, Iowa City, Iowa

[21] Appl. No.: 436,607

[22] Filed: Dec. 13, 1982

[51] Int. Cl.³ ............................................. A61B 17/06
[52] U.S. Cl. .................................................... 128/340
[58] Field of Search ............... 128/334 R, 334 C, 340, 128/346, 335

[56] References Cited

U.S. PATENT DOCUMENTS

| | | | |
|---|---|---|---|
| 640,853 | 1/1900 | Arnold | 128/340 |
| 659,422 | 10/1900 | Shidler | 128/340 |
| 2,704,541 | 3/1955 | Wyatt | 128/303 R X |
| 2,738,790 | 3/1956 | Todt et al. | 128/334 R |
| 3,349,772 | 10/1967 | Rygg | 128/340 |
| 3,608,539 | 9/1971 | Miller | 128/314 X |
| 3,763,860 | 10/1973 | Clarke | 128/334 R X |
| 3,946,740 | 3/1976 | Bassett | 128/334 R |
| 4,244,370 | 1/1981 | Furlow et al. | 128/303 R |
| 4,263,903 | 4/1981 | Griggs | 128/334 R X |
| 4,345,600 | 8/1982 | Rothfuss | 128/334 R |
| 4,349,027 | 9/1982 | Di Francesco | 128/303 R |
| 4,400,878 | 8/1983 | Vaudreuil | 30/329 |

Primary Examiner—Michael H. Thaler
Attorney, Agent, or Firm—Zarley, McKee, Thomte, Voorhees & Sease

[57] ABSTRACT

The device of the present invention comprises an elongated tube which is adapted to be inserted into the body so that its internal end is positioned adjacent the tissue which is to be sutured. A plunger is sized to slide within the tube and includes at one end a grasping mechanism for releaseably grasping a pair of needles in spaced-apart relation to one another. The plunger is fitted within the tube and the needles are forced outwardly through the lower end of the tube so that they penetrate and extend through the tissue to be sutured. The needles are forced through the tissue to be sutured and are forced outwardly through the skin layer of the patient so that they can be grasped and pulled from the releaseable grasping mechanism of the plunger.

7 Claims, 18 Drawing Figures

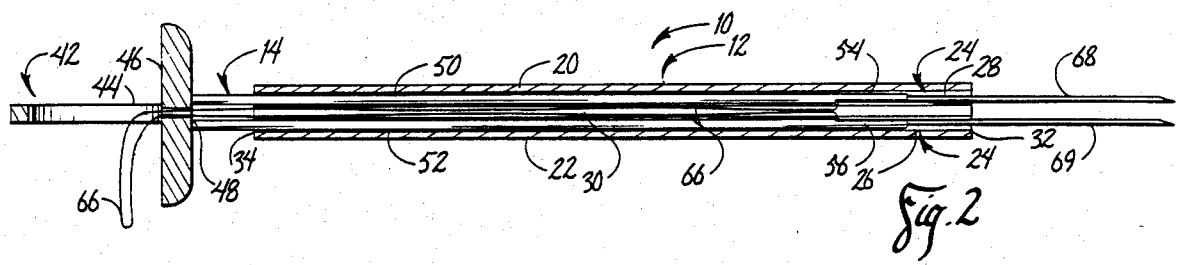
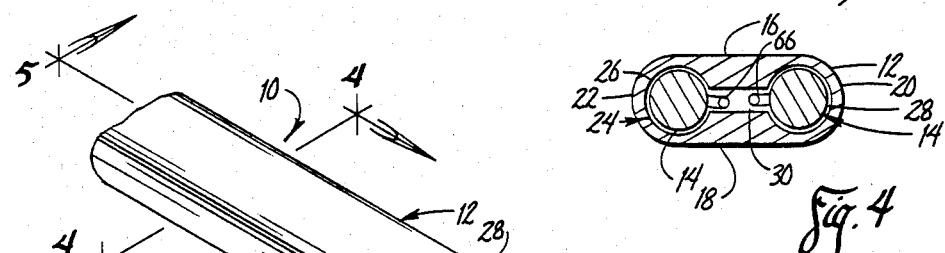
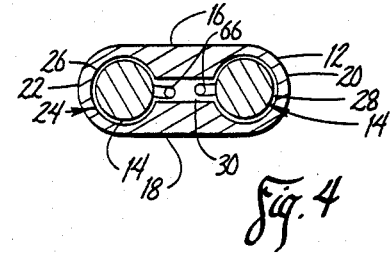
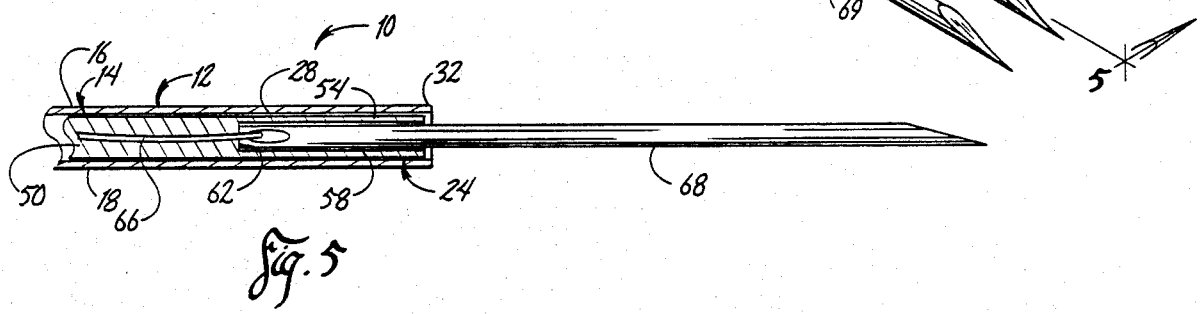
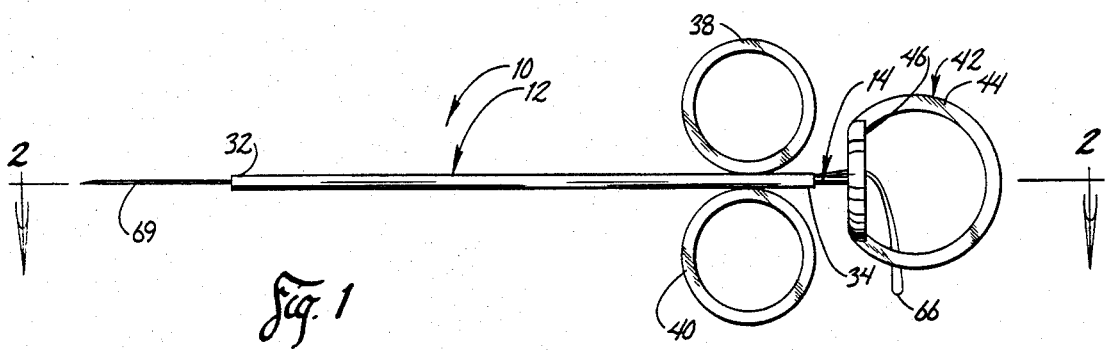

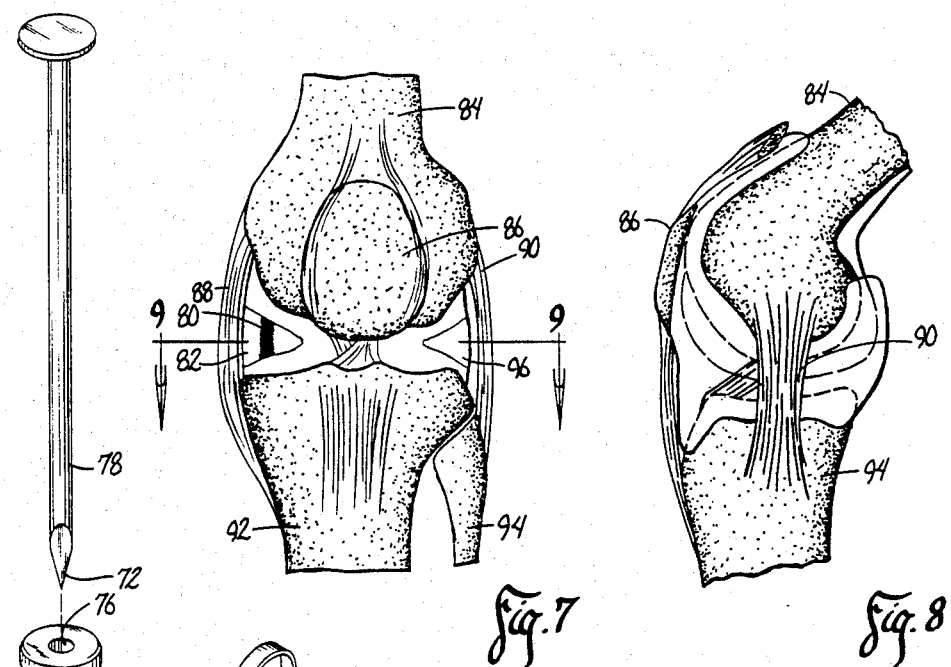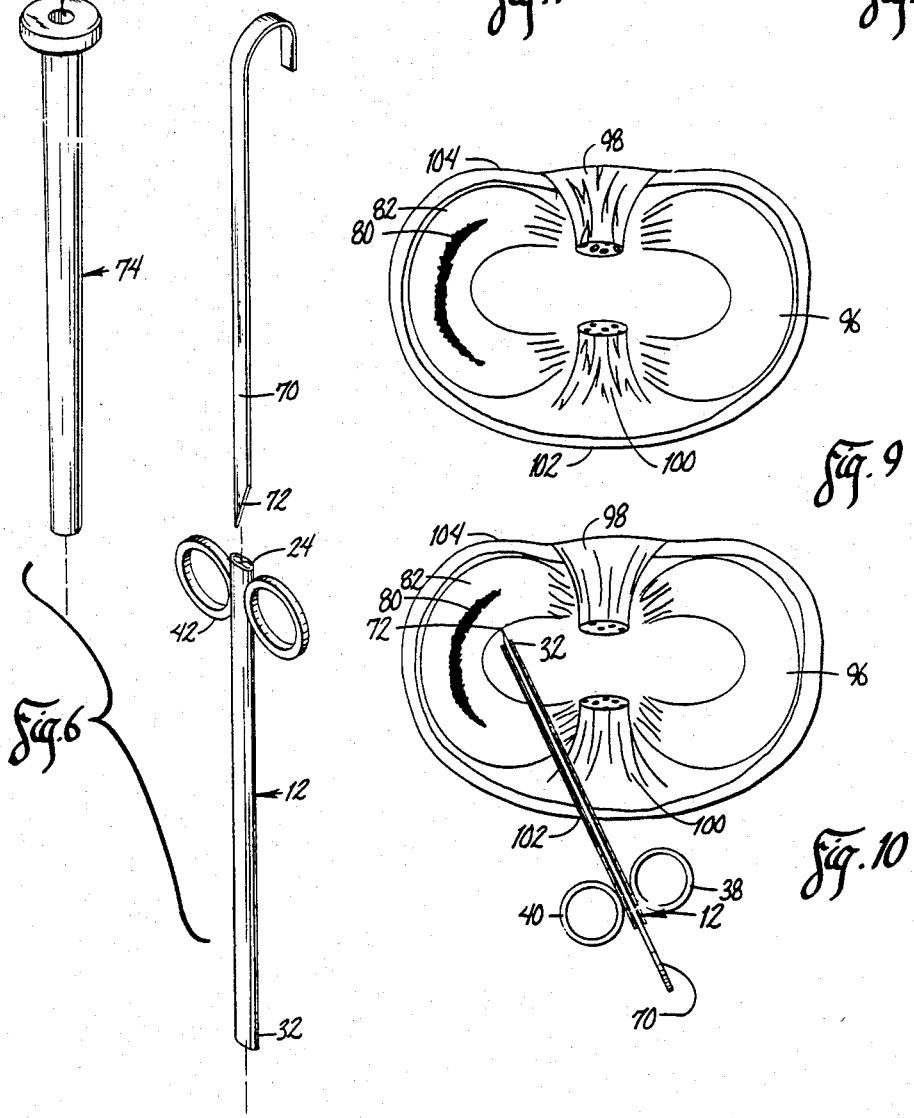

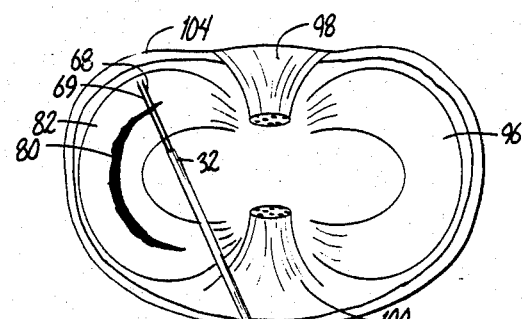
fig.11
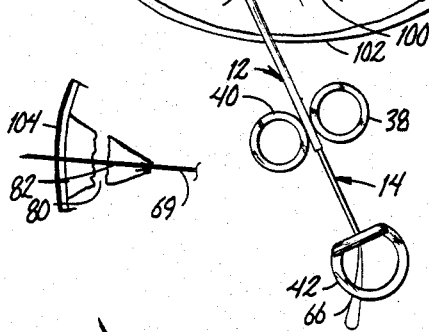
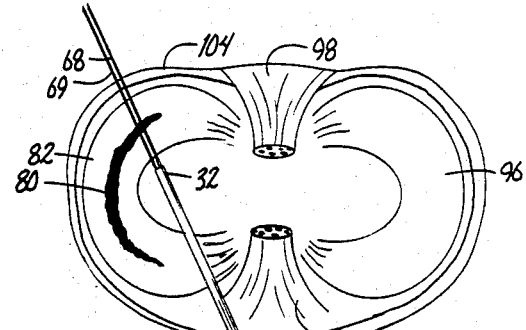
fig.12
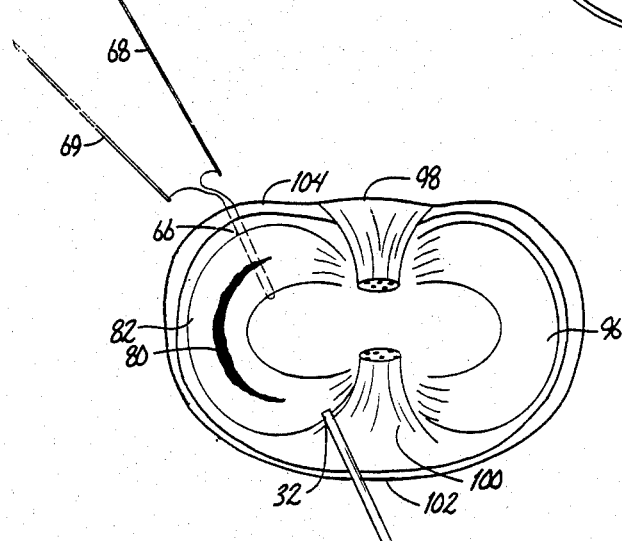
fig.13
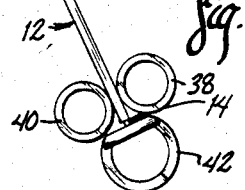
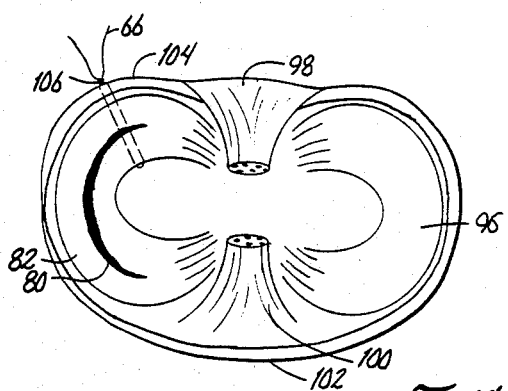
fig.14
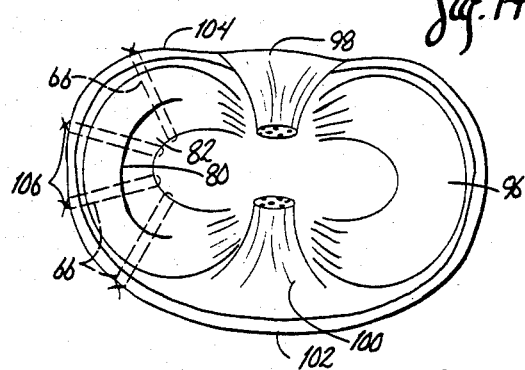
fig.15

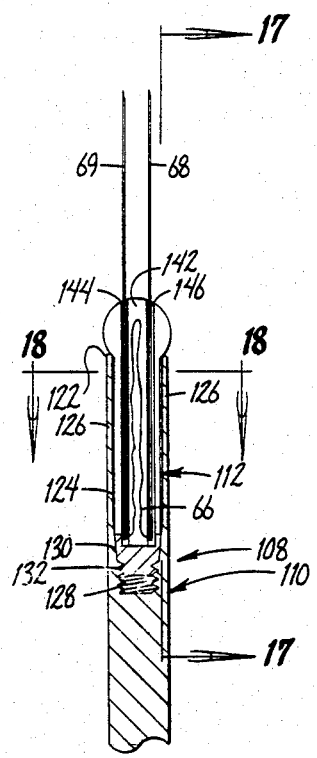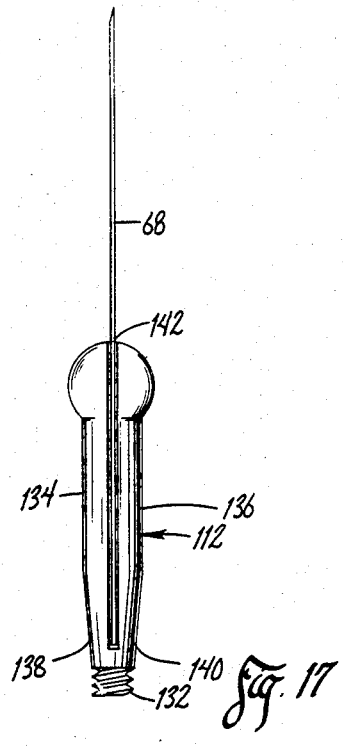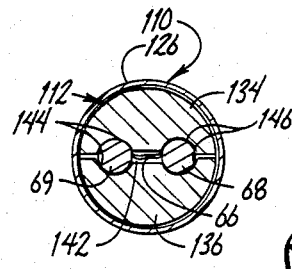

SUTURING DEVICE AND METHOD FOR USING SAME

BACKGROUND OF THE INVENTION

This invention relates to a suturing device and method for using same. The invention relates particularly to surgical techniques for use in knee surgery, although the invention may also be used in other types of surgery.

One injury which commonly occurs within the knee joint is the tearing or parting of the meniscus or cartilege within the knee. When this tearing occurs, surgical techniques are often necessary to alleviate the problems caused by the injury. Usually, these surgical techniques involve the removal of all or a portion of the torn meniscus. While these techniques alleviate discomfort and malfunction of the knee joint, they often result in additional irritation and grating of the various moving parts of the knee joint. Over a long period of time, this irritation can result in arthritis.

In recent years, the surgical techniques used for the above operation have involved the use of an arthroscope which permits the surgery to be accomplished without large incisions in the knee. One or more small openings, approximately 4½ millimeters in diameter, are made in the skin layer so as to provide access for an elongated sleeve. The sleeve is inserted through the surgical opening and the instruments for performing the surgical techniques are inserted through the tube to the point where the surgery is to be accomplished. Furthermore, the use of fiber optics which are also inserted through the tube, permits the surgeon to see the area where the surgery is necessary without the need for making a large incision to permit visual inspection.

Therefore, a primary object of the present invention is the provision of an improved surgical device for suturing torn tissue and an improved method for using the same.

A further object of the present invention is the provision of a suturing device which will permit the reapproximation of the separated edges of a torn meniscus of the knee to allow healing of the injured tissue without making a large incision to expose the joint structures.

A further object of the present invention is the provision of a device which permits the surgeon to apply substantial force to the needle, so that the needles can be inserted through the tough tissue of the torn meniscus.

A further object of the present invention is the provision of a suturing device which can be utilized in combination with present day arthroscope surgical techniques.

A further object of the present invention is the provision of a suturing device which permits the penetration of two needles having a thread extending therebetween into and through the torn meniscus and outwardly through the exterior skin layer of the knee where it can be grasped manually.

A further object of the present invention is the provision of a surgical device which permits the suturing of the meniscal tear with a mattress suture which is inserted from the inside of the joint and secured with a knot located beneath the exterior skin layer of the knee.

A further object of the present invention is the provision of a device which is economical to manufacture, durable in use and efficient in operation.

SUMMARY OF THE INVENTION

The present invention is a new medical device which will reapproximate the separated edges of a torn meniscus of the knee to allow healing of the injured tissue without making a large incision to expose the joint structures. This instrument includes a needle holder or plunger which will releaseably hold two needles in spaced apart relation; and a hollow outer sleeve which can be inserted into the knee and which can receive the needle holder for sliding movement therein. The plunger is capable of driving the needles and the attached suture out of the inner end of the sleeve and into the appropriate tissues. The plunger holds two cylindrical surgical needles which in turn are attached to each end of a single absorbable suture. Loaded with its needles and suture, the outer sleeve can be inserted between the body surfaces of the knee joint and have its inner end placed adjacent the edge of the desired portion of the meniscus. When the plunger is depressed, the two needles are simultaneously driven through the meniscus and the joint capsule to the exterior of the skin layer of the joint. At that point, they can be grasped manually and pulled away from the plunger and outwardly from the knee joint. The surgical thread can then be tied externally of the knee joint to complete the mattress joint.

The present invention permits the repairing of tears of the meniscus in the human knee from inside of the joint and under direct view of an arthroscopic system. Presently any attempts at repair of the meniscal tears are done very selectively from the outside inward, requiring large surgical exposure.

The present invention differs from the prior art in that it allows a mattress suture to be inserted from inside the joint and secured with a knot located on the exterior of the joint. Presently all of the existing arthroscopic surgical instruments are designed for cutting or shaving tissues away from the inside of the joint and not for reconstructing damaged tissues.

The needle holder apparatus of the present invention can be formed in a number of different ways. Two of the preferred ways are shown in the present invention. One embodiment is flat in cross-section and is designed to fit into its own introducer sleeve to allow insertion through its own portal in the knee joint for use in the triangulation method of arthroscopic surgery. In the triangulation method the arthroscope and the surgical instrument for manipulating objects are placed in separate portals in the knee. This unit includes a flattened cylindrical sleeve allowing the separation of the needles to be wider, yet allowing entry into narrower joint spaces. This modification has the disadvantage that it is more difficult to choose the plane of the mattress suture, but it has the advantage that it will provide access to the far reaches of tighter fitting joints.

Another version of the needle holder invoves a round holder and sleeve which allows the surgeon to rotate the position of the needle so that the desired plane of the mattress suture can be made to fit the needs of the situation.

It is contemplated that either of the above needle holders could be modified by providing curvature to the left or right in varying degrees to provide easy access through a single portal to remote areas of the meniscus. It is also possible to utilize a tool which inserts only a single needle as opposed to the two spaced apart needles described above.

BRIEF DESCRIPTION OF THE FIGURES OF THE DRAWINGS

FIG. 1 is a top plan view of the surgical device of the present invention.

FIG. 2 is a sectional view taken along line 2—2 of FIG. 1.

FIG. 3 is an enlarged perspective view of one end of the device shown in FIG. 2.

FIG. 4 is a sectional view taken along line 4—4 of FIG. 3.

FIG. 5 is a sectional view taken along line 5—5 of FIG. 3.

FIG. 6 is an exploded perspective view of two portal opening devices utilized with the present invention.

FIG. 7 is a front view of a knee joint illustrating a torn meniscus.

FIG. 8 is a side view of a knee joint.

FIG. 9 is a top sectional view of a knee joint taken along line 9—9 of FIG. 7.

FIG. 10 is a view similar to FIG. 9 showing one of the portal opening devices of FIG. 6, inserted within the knee joint.

FIGS. 11-15 are views similar to FIG. 10 showing the various steps of the process utilizing the surgical device of the present invention.

FIG. 16 is a sectional view of a modified form of the present invention.

FIG. 17 is a sectional view taken along line 17—17 of FIG. 16.

FIG. 18 is a sectional view taken along line 18—18 of FIG. 16.

DETAILED DESCRIPTION OF THE PREFERRED EMBODIMENT

Referring to the drawings, the numeral 10 generally refers to the suturing device of the present invention. Device 10 comprises a tubular member or sleeve 12, and a plunger 14. Sleeve 12 is in cross-section ovular in shape, having an upper flat surface 16, a lower flat surface 18, and opposite rounded sides 20, 22. Sleeve 12 includes an elongated bore 24 extending longitudinally therethrough. As seen in FIG. 4, bore 24 includes in cross-section a pair of spaced apart round passageways 26, 28 which are interconnected by a central flat passageway 30. Passageway 30 provides communication between passageways 26, 28 along the entire length thereof. Sleeve 12 includes a distal end 32 and an inlet end 34. Fixed to the exterior of end 34 are a pair of finger receiving rings 38, 40.

Plunger 14 comprises a handle 42 which is made up of a thumb ring 44 and a circular thumb pad 46 which is fixed to thumb ring 44. Pad 46 has a radially extending slot 48 therein for receiving the suture thread in a manner to be described more fully hereafter. Fixed to the opposite side of pad 46 from thumb ring 44 are a pair of rods or shafts 50, 52 which are spaced apart in parallel relation and which have distal ends designated by the numerals 54, 56, respectively. Preferably the length of shafts 50, 52 is approximately equal to the length of tubular member 12. Distal ends 54, 56 are formed into hollow sleeves or receptacles 58, 60 which terminate in inner solid ends 62. Extending along the lengths of receptacles 58, 60 are inwardly extending slots 64 which provide two functions. Slots 64 permit slight flexion of the walls of receptacles 58, 60 and slots 64 also provide means for receiving the suture thread 66 attached to a pair of needles 68, 70. Thus, needles 68, 70 may be frictionally fitted within receptacles 58, 60 with the suture thread 66 passing through the slots 64 as shown in FIG. 3.

Shafts 50, 52 are sized to fit within the round passageways 26, 28 and to slide therein as shown in FIGS. 1-3. The needles 68, 70 are placed within the receptacles 54, 56 as also shown in FIG. 3.

Cutting tools are shown in FIG. 6 for use with the method of the present invention. One tool is designated by the numeral 70 and is adapted to fit within tubular sleeve 12 shown in FIGS. 1-5. Cutting tool 70 is J-shaped, and is flat in cross-section, containing a sharpened cutting edge 72 at its lower end. When tool 70 is slidably inserted within tube 12, the cutting edge 72 protrudes beyond the lower end of tube 12, thereby providing a cutting edge for insertion into the knee joint upon which the surgery i to be accomplished.

Also shown in FIG. 6 is a round tube or sleeve designated by the numeral 74. Sleeve 74 is round in cross-section and includes a round tubular passageway 76 extending along the length thereof. Tube 74 is adapted for use with the tool shown in FIGS. 16-18. A corresponding cutting tool 78 is sized to fit within bore 76 in the same manner that tool 70 fits within sleeve 12.

FIGS. 7, 8 and 9 show a typical knee joint having a tear 80 in the medial meniscus 82. For purposes of reference, the various anatomical parts of the knee joint include the femur 84, the patella or knee cap 86, the medial collateral ligament 88, the lateral collateral ligament 90, the tibia 92, and the fibula 94. The numeral 96 designates the lateral meniscus, and the numerals 98, 100 designate the posterior and anterior cruciate ligaments, respectively. The numeral 102 designates the front skin layer of the knee joint, and the numeral 104 designates the rear skin layer of the knee joint.

The suturing device of the present invention is used in the following manner. Cutting tool 70 is fitted within the bore 24 of tubular member or sleeve 12. The cutting edge 72 protrudes outwardly beyond the lower end 32 of tubular member 12. The surgeon uses the cutting edge 72 to form an opening or portal in front skin layer 102 as shown in FIG. 10. The cutting tool and the tube are inserted through the portal until the distal end 32 of the sleeve 12 is adjacent meniscus 82, all as shown in FIG. 10. Cutting tool 70 is then withdrawn from sleeve 12 and plunger 14 is inserted therein. Prior to insertion of plunger 14 into sleeve 12, needles 68, 69 are inserted in receptacles 58, 60 and the thread 66 interconnecting needles 68, 69 is fitted within slot 48 of thumb pad 46 in the manner shown in FIG. 11.

Plunger 42 is then forced downwardly through bore 24 in sleeve 12 until the needles 68, 69 engage meniscus 82. At this point, the surgeon applies pressure to handle 42 to force the needle 69 through meniscus 82 so as to cross and connect the opposite sides of tear 80 in the manner shown in FIG. 12. The needles 68, 69 are forced outwardly through rear skin layer 104 so that their ends are free for grasping by the surgeon.

The surgeon grasps the ends of needles 68, 69 and pulls the needles outwardly from receptacles 58, 60 of plunger 14. He continues to pull the needles outwardly through rear skin layer 104 until the needles have completely passed through cartilege 82 in the manner shown in FIG. 13. Because needles 68, 70 are spaced apart at the time they pass through cartilege or meniscus 82, the thread 66 is looped through the two spaced apart holes formed by the needles in the manner shown in FIG. 13.

Furthermore, the central passageway 30 which interconnects and provides communication between round passageways 26, 28, permits the thread 66 to be drawn through the interior of bore 24 in sleeve 12 so that it can be drawn tightly against meniscus 82 so as to draw the opposite jagged edges of tear 80 together. The surgeon ties a knot 106 in the manner shown in FIG. 14, thereby providing a single mattress suture holding the opposite edges of tear 80 together.

The process is repeated as many times as necessary to provide different stitches so as to suture tear 80 along its entire length. An example of a typical group of mattress sutures formed by this process is shown in FIG. 15. The present device is meant to be used in connection with an arthroscope so that the surgeon can see the interior of the joint during the time that the sutures are being formed. This enables the surgeon to position the interior end 32 of tube 12 in the proper position for forming the suture at the desired location. The arthroscope may be inserted into the interior of the joint through a separate portal (not shown) or the arthroscope itself may be used in the place of tube 12. Presently known arthroscopes include both a sleeve for the insertion of tools and an optic tube for providing vision into the interior of the joint. In such a case, the arthroscope would be inserted in the place of tube 12, and the plunger 14 would be inserted through the work tube of the arthroscope.

Referring to FIGS. 16-18, a modified form of the invention is shown which is particularly adapted for use with an arthroscope or with a round tube or sleeve such as designated by the numeral 74, in FIG. 6. The device is designated generally by the numeral 108 and includes a plunger body 110 and a plunger head 112 adapted to receive needles 68, 69. Plunger body 110 includes a handle 114 formed from a thumb plate 116 and a thumb ring 118. Plunger body 110 includes a shank 120 which terminates in a hollow end 122. End 122 is provided with a threaded opening 124 having cylindrical sidewalls 126. The inner end of threaded opening 124 is provided with threads 128 and with a tapered cam 130.

Plunger head 112 is provided with a threaded lower end 132 adapted to be threadably received within threads 128. Referring to FIG. 17, plunger head 112 includes two upwardly extending bifurcated members 134, 136 which are flexible so as to be capable of moving toward and away from one another. The lower ends of members 134, 136 are provided with tapered cam followers 138, 140 which are adapted to engage cams 130 during threadable insertion of plunger head 112 into threaded opening 124.

Bifurcated members 134, 136 are separated by a slot 142. The interior facing surfaces of bifurcated members 134, 136 are provided with arcuate grooves 144, 146 which are in registered alignment with one another, and which together form circular bores for receiving needles 68, 69.

To assemble device 108, one places needles 68, 69 within the circular grooves formed by grooves 144, 146. As can be seen in FIG. 16, the thread 66 which interconnects the needles 68, 69 is positioned in slot 142 between the spaced apart needles 68, 69. Slot 142 permits thread 66 to be dawn out of plunger head 112 when the needles 68, 69 are drawn out of the plunger.

After needles 68, 69 are placed within head 112, head 112 is threadably inserted into threaded opening 124 of plunger body 110. Cam followers 138, 140 slide against cam 130 during threaded insertion, thereby camming the bifurcated members 134, 136 toward one another so as to cause them to firmly grasp needles 68, 69 therebetween.

Once assembled, the device 108 is used in a manner similar to that shown in FIGS. 11-15. The device may be inserted through a circular tube such as 74 shown in FIG. 6, or it can be inserted through the circular tube provided in presently known arthroscopes. Once the needles have been forced through the cartilege to the position shown in FIG. 12, they may be released from device 108 by rotating plunger body 110 in a direction which causes unthreading of plunger head 112 from plunger body 110. This is possible due to the fact that the needles are embedded in the cartilege and are not free to rotate in unison with the plunger body 110. When plunger head 112 has been unthreaded sufficiently to permit the flexible bifurcated members 134, 136 to separate, the needles are released and can be pulled through the rear skin layer 104 in the manner shown in FIG. 13.

The device shown in FIGS. 1 through 15 has the advantage that it is flat and thin and can be inserted easily into a knee joint which is tight. It does have the disadvantage that the receptacles 58, 60 can be sized for only a single size needle. If different sized needles are desired, it is necessary to have separate instruments sized to fit each needle. The solid inner ends of receptacles 58, 60 permit the surgeon to apply substantial force to the needles so as to cause the needles to penetrate through the cartilege. The slots 64 in receptacles 58, 60 however, provide sufficient flexibility to the receptacles 58, 60 to permit the needles to be easily pulled from the receptacles for the final step of the process shown in FIG. 13.

The device shown in FIGS. 16-18 has the advantage that it can accommodate needles of differing sizes. The camming action of bifurcated members 134, 136 permits the device to tightly grip needles of various diameters. Furthermore, the device shown in FIGS. 16-18 is more readily adapted to the working tube of arthroscopes currently being used.

Thus, it can be seen that the device accomplishes at least all of its stated objectives.

What is claimed is:

1. A method for suturing torn cartilege located internally of a patient's knee, said knee having a forward external skin layer and a rear skin layer located on opposite sides of said torn cartilege, said method comprising inserting an elongated tube having internal and external ends through a surgically prepared opening in said forward skin layer of said knee, said tube having in cross section an ovular shape with an upper surface, a lower surface, and opposite rounded sides which define a completely enclosed longitudinal bore having open opposite ends and having in cross section a pair of spaced apart round passageways and a central flat passageway providing communication between said round passageways along the entire length thereof;

positioning said tube with its internal end adjacent said torn cartilege and its external end located outside said forward skin layer;

detachably securing a pair of needles in parallel spaced apart relation to one another to one end of a plunger, said needles being interconnected by a surgical thread;

slidably inserting said needles into said round passageways of said bore until said needles are protruding from said internal end of said tube and are in contact with said torn cartilege, and at least a portion of said plunger and said surgical thread are outside said external end of said tube;

manually forcing said needles through said torn cartilege and said rear skin layer by exerting pressure on said portion of said plunger located externally of said tube until at least a portion of each of said needles is protruding externally of said rear skin layer;

detaching said needles from said plunger;

grasping said protruding portions of said needles and pulling them completely through said torn tissue and said rear skin layer whereby said surgical thread is pulled completely through said central passageway of said bore and is looped through the two holes formed by said needles in said torn cartilege and has two free ends located externally of said rear skin layer;

tying said two free ends of said thread together externally of said rear skin layer.

2. A surgical device according to claim 1 wherein said plunger means comprises a pair of elongated shafts each sized to fit within and slide within one of said said spaced apart longitudinal passageways.

3. A surgical device according to claim 2 wherein said needle grasping means comprise a pair of needle receptacles, each located at one end of one of said shafts, each of said needle receptacles being sized to frictionally receive one end of one of said needles.

4. A surgical device according to claim 3 wherein said central passageway provides access for said thread to interconnect said two needles when said needles are within said grasping means and said grasping means is within said bore of said tubular member.

5. A surgical device according to claim 4 wherein each of said needle receptacles comprise an elongated cylindrical cavity in said one end of one of said shafts, said cylindrical cavity having one of its cylindrical ends open for receiving one of said needles and the other of its cylindrical ends having a solid end wall for engaging said needle and imparting axial movement to said needle when said plunger moves from said retracted to said extended positions.

6. A surgical device for suturing torn cartilege within a patient's knee comprising:

an elongated tubular member having an internal end adapted to be positioned in the proximity of the cartilege to be sutured and an external end;

finger receiving means on said tubular member adjacent said external end thereof;

said tubular member having in cross section an ovular shape with an upper surface, a lower surface and opposite rounded sides defining a completely enclosed elongated bore extending longitudinally through said tubular member, said bore having opposite open ends and comprising in cross section a pair of spaced apart elongated needle passageways, and a central passageway positioned between said needle passageways and providing communication therebetween along the entire length thereof;

a pair of surgical needles each having a pointed end and a rearward end and each being fitted within one of said needle passageways with said pointed end pointing toward said internal end of said tubular member, said needles being longitudinally slidable within said needle passageways;

a suturing thread operatively connected to both of said needles adjacent said rearward ends of said needles, at least a portion of said thread extending outside said external end of said tubular member;

plunger means having a handle and a needle grasping means, said needle grasping means releaseably holding said needles and being adapted to release said needles in response to manual pulling of said needles away from said grasping means;

said handle being located externally of said bore for permitting the application of axial manual pressure between said handle and said finger receiving means of said tubular member to cause said needles to be forced longitudinally through said bore and outwardly through said internal end of said tubular member, said central passageway permitting said suturing thread to pass through said bore with said needles.

7. A surgical device for suturing a torn cartilege within a patient'knee comprising:

an elongated tubular member having an internal end adapted to be positioned in the proximity of the cartilege to be sutured and an external end;

said tubular member having an elongated bore extending longitudinally through said tubular member, said bore having opposite open ends;

plunger means telescopically fitted within said elongated bore for longitudinal sliding movement therein, said plunger means comprising an elongated body member, and a plunger head;

said body member having a handle at one end thereof and being provided at the opposite end with a threaded opening having cylindrical sidewalls, said cylindrical sidewalls being provided with a tapered cam means which is within said opening;

said plunger head comprising a threaded end portion and a pair of spaced apart bifurcated members which are yieldably movable toward and away from one another;

a pair of spaced apart needles positioned in the space between said bifurcated members and having pointed ends protruding outwardly therefrom;

surgical thread being connected to both of said needles;

said plunger head being threadably insertable into said threaded opening whereby said cam means engages said bifurcated members and forces said bifurcated members toward one another so as to retentively engage said needles therebetween;

said bifurcated members being movable apart from one another when said plunger head is removed from said threaded opening so as to release said needles from retentive engagement between said bifurcated members.

* * * * *